United States Patent
Gelmont et al.

(10) Patent No.: US 9,309,377 B2
(45) Date of Patent: Apr. 12, 2016

(54) FLAME RETARDANTS, PROCESSES FOR THEIR PREPARATION AND USES THEREOF IN POLYURETHANE AND POLYISOCYANURATE FOAMS

(71) Applicant: BROMINE COMPOUNDS LTD., Beer Sheva (IL)

(72) Inventors: Mark Gelmont, Haifa (IL); Michael Yuzefovich, Haifa (IL); Dorit Peled, Haifa (IL); Orly Cohen, Kiryat Tivon (IL); Ron Frim, Haifa (IL)

(73) Assignee: BROMINE COMPOUNDS LTD., Be'er-Sheva (IL)

( * ) Notice: Subject to any disclaimer, the term of this patent is extended or adjusted under 35 U.S.C. 154(b) by 0 days.

(21) Appl. No.: 14/247,574

(22) Filed: Apr. 8, 2014

(65) Prior Publication Data

US 2014/0303271 A1    Oct. 9, 2014

Related U.S. Application Data

(63) Continuation-in-part of application No. PCT/IL2012/000356, filed on Oct. 9, 2012.

(60) Provisional application No. 61/545,155, filed on Oct. 9, 2011.

(51) Int. Cl.

| | |
|---|---|
| *C08G 18/50* | (2006.01) |
| *C08K 5/06* | (2006.01) |
| *C07C 43/178* | (2006.01) |
| *C09K 21/14* | (2006.01) |
| *C08G 18/66* | (2006.01) |
| *C08G 18/76* | (2006.01) |
| *C08G 18/40* | (2006.01) |
| *C08G 18/48* | (2006.01) |
| C08G 101/00 | (2006.01) |

(52) U.S. Cl.
CPC .............. *C08K 5/06* (2013.01); *C08G 18/4018* (2013.01); *C08G 18/4804* (2013.01); *C08G 18/5012* (2013.01); *C08G 18/6611* (2013.01); *C08G 18/6618* (2013.01); *C08G 18/6674* (2013.01); *C08G 18/6685* (2013.01); *C08G 18/7664* (2013.01); *C09K 21/14* (2013.01); *C07C 43/1786* (2013.01); *C08G 2101/0008* (2013.01); *C08G 2101/0025* (2013.01)

(58) Field of Classification Search
CPC .................. C08G 18/5012; C07C 43/1786
See application file for complete search history.

(56) References Cited

U.S. PATENT DOCUMENTS

| | | | |
|---|---|---|---|
| 4,067,911 A | | 1/1978 | Walraevens et al. |
| 4,069,207 A | | 1/1978 | Klein |
| 4,211,730 A | * | 7/1980 | Vollkommer et al. ...... 526/219.6 |
| 6,924,332 B2 | * | 8/2005 | Onishi et al. ................ 524/189 |
| 2005/0079442 A1 | * | 4/2005 | Dueber et al. ............ 430/270.1 |
| 2005/0124746 A1 | | 6/2005 | Zilberman et al. |
| 2005/0124829 A1 | * | 6/2005 | Beruben ....................... 560/254 |
| 2007/0276055 A1 | * | 11/2007 | Sjerps ............................ 521/85 |

FOREIGN PATENT DOCUMENTS

| | | |
|---|---|---|
| CN | 1625540 | 6/2005 |
| CN | 1957041 | 5/2007 |
| DE | 3 320 333 | 1/1984 |
| EP | 0 047 866 | 3/1982 |
| EP | 0 481 126 | 4/1992 |
| WO | 03/064361 | 7/2003 |
| WO | 2005/118720 | 2/2004 |
| WO | WO 2005/118720 | 12/2005 |

OTHER PUBLICATIONS

Phosflex 31L Information. ICL Industrial Products. http://icl-ip.com/products/phosflex-31L/. As viewed on Mar. 19, 2015.*
International Search Report for PCT/IL2012/000356, mailed Jan. 2, 2013.
Written Opinion for PCT/IL2012/000356, mailed Jan. 2, 2013.
Office Action dated Feb. 11, 2015, issued in Chinese App. No. 201280060629.4 (with partial English translation).
Extended European Search Report issued in Application No. 12840704.6 dated Sep. 25, 2015.

* cited by examiner

*Primary Examiner* — Randy Gulakowski
*Assistant Examiner* — Stephen Rieth
(74) *Attorney, Agent, or Firm* — Nixon & Vanderhye P.C.

(57) ABSTRACT

The invention provides pentabromobenzyl moiety containing hydroxy-functional compounds which are useful as flame-retardants in flexible and rigid polyurethane foams and also in rigid polyisocyanurate foams. Processes for preparing the compounds, polyurethane and polyisocyanurate foams containing the compounds are also provided by the invention.

20 Claims, No Drawings

FLAME RETARDANTS, PROCESSES FOR THEIR PREPARATION AND USES THEREOF IN POLYURETHANE AND POLYISOCYANURATE FOAMS

This application is a continuation-in-part of International Application No. PCT/IL2012/000356 filed Oct. 9, 2012 which designated the U.S. and claims the benefit of U.S. Provisional Application No. 61/545,155 filed Oct. 9, 2011, the entire contents of each of which are hereby incorporated by reference.

FIELD OF THE INVENTION

The present invention provides novel pentabromobenzyl moiety containing hydroxy-functional compounds serving, either with or without the addition of known commercial flame retardants, as highly efficient reactive flame retardants in urethane systems, particularly in flexible and rigid polyurethane foams or rigid polyisocyanurate (PIR) foams.

BACKGROUND OF THE INVENTION

Brominated flame-retardants are known to be highly effective and in many cases are the only option for reducing the fire risk of synthetic materials such as rigid or flexible polyurethane foams. However, the growing concern regarding health and ecological issues has led inventors to develop a new reactive macro-molecular flame retardant.

Environmental and health problems diminish if a flame retardant is either reacted into the polymer matrix and cannot be leached-out, or if the flame retardant has a sufficiently high molecular weight that it does not volatize, and is not likely to bio-accumulate in living tissues.

Compounds containing a pentabromobenzyl moiety are known as flame retardants. Pentabromobenzyl acrylate (EP 481126), pentabromobenzyl terephthalate (DE 33 20 333), and pentabromobenzyl tetrabromophthalate (EP 47866) are reported to be used in flame retardant polymer compositions.

Low molecular weight pentabrombenzyl alkyl ethers containing one hydroxide group are described in US 2005/0124746. According to said publication, pentabromobenzyl alkyl ethers are prepared by the reaction of a pentabromobenzyl halide (PBBBr) with an aliphatic mono or di-alcohol (or the corresponding metal alcoholate), in the presence or absence of a base. Aliphatic diols (or the corresponding metal alcoholate) are reacted with a pentabrombenzyl halide, preferably PBBBr, to obtain the pentabrombenzyl ethers with one functional —OH group (Formula A).

Formula A

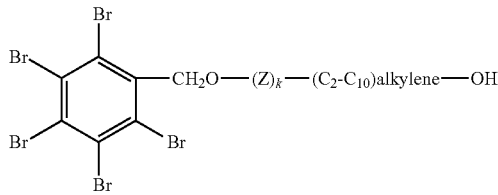

Z=linear or branched —[($C_2$-$C_8$)alkylene-O]$_n$
n represents an integer from 2 to 4
k may be 0 or 1.

SUMMARY OF THE INVENTION

The present invention provides novel reactive pentabromobenzyl moiety containing hydroxy-functional compounds possessing highly satisfactory flame retarding characteristics and having good compatibility with the polyol components of the polyurethane system. The invention further provides polyurethane and polyisocyanurate compositions comprising said novel pentabromobenzyl moiety containing hydroxy-functional compounds that exhibit excellent fire retardancy.

The flame-retardant of the present invention possesses two useful properties, in addition to its high efficacy as a flame retardant: it is both fully reactive through its hydroxyl-functional groups, and is a macro-molecular polymer of up to 3000. This means that the flame retardant of the invention becomes integrated into the polymer substrate, such as a rigid or flexible foam, so that it is not released to the environment and the large molecules are not likely to penetrate through cell membranes of living tissue, and therefore does not pose a health hazard.

The present invention concerns the class of flame retardants obtainable by reacting pentabromobenzyl bromide (chemically named 1,2,3,4,5-pentabromo-6-bromomethylbenzene) with polymeric polyols having a number of hydroxyl groups that is not less than 3 (with a preferred molecular weight from ~250 to 3000, more preferably from ~250 to 1000, or a mixture of such polyols (see Scheme 1 below)). The polyol utilized as a starting material in the present invention is a branched polyol having n branches (n is an integer equal to or greater than 3) with n hydroxyl groups, e.g., terminal hydroxyl groups according to the formula Z(OH)n, wherein Z is the branched moiety, which is preferably a branched hydrocarbon including ether linkages, with the molecular weight of Z being between 150 and 3000 Da.

It is noted that the branched polyol contains n hydroxyl groups available for the reaction with pentabromobenzyl bromide. However, the molar ratio between the polyol and the pentabromobenzyl bromide is adjusted such that in the product which is formed some branches are terminated with the pentabromobenzyl group and other branches with the original hydroxyl groups. In this way, a polymeric flame retardant is obtained which carry significant amounts of bromine and is still reactive in polyurethane systems due to the presence of hydroxyl groups. The compounds of the invention are generally liquids, e.g., viscous liquids, and are preferably characterized by bromine content between 10 and 65 wt % and hydroxyl value in the range from 20 mg KOH/g to 120 mg KOH/g.

Thus, in one aspect, the invention provides compounds which are pentabromobenzyl alkyl ether containing hydroxyl functionality of Formula 1:

Formula 1

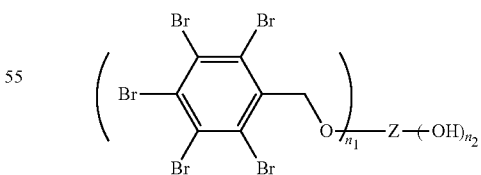

wherein each of $n_1$ and $n_2$ is an integer equal to or greater than 1, with their the sum being equal to or greater than 3, and Z is a moiety derived from a branched polyol and is preferably a moiety containing n branches ($n=n_1+n_2$), wherein each branch consists of a chain that includes ether linkages, e.g., a chain comprising not less than 3 repeating units (e.g., not less than 5 repeating units) which are preferably alkylene oxide units. More preferably, Z has the following structure (Formula 2):

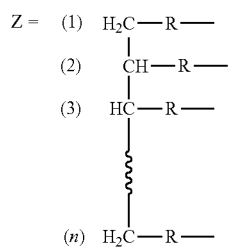

wherein R is selected from the group consisting of:
O—[($C_2$-$C_3$)alkylene-O]$_m$—(($C_2$-$C_3$)alkylene and
O—[$CO_4C_2$-$C_5$)alkylene-O]$_m$—(($C_2$-$C_5$)alkylene, m≥3
(e.g., m≥5), and n is an integer from 3 to preferably 6.

For example, a compound of the invention having three branches (i.e., n=3), with each branch consisting of a chain that includes ether linkages with the repeating unit being —[$CH_2$—$CH_2$—O], wherein two branches are terminated with pentabromobenzyl group (abbreviated —$CH_2$—$C_6Br_5$) and one branch is terminated with hydroxyl group (i.e., $n_1$=2 and $n_2$=1), is represented by the following formula:

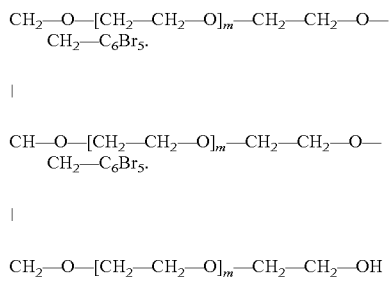

One convenient way for preparing the compounds of Formula 1 is illustrated by the reaction scheme depicted in Scheme 1:

Scheme 1:

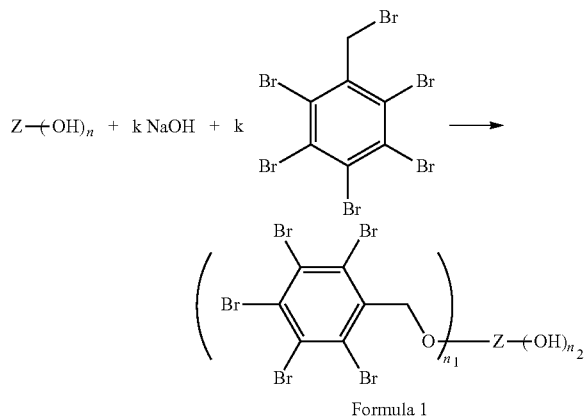

Formula 1 n ≥ 3
1 ≤ k < n;
$n_1$ = 1,...n − 1
$n_2$ = n − $n_1$ wherein:
$n_1$—indicates the number of pentabromobenzyl groups, and is an integer from 1 to n−1;
$n_2$—indicates the number of hydroxyl groups, and is an integer from n−1 to 1; such that the total number of pentabromobenzyl groups and hydroxyl groups in the compound of the invention is not less than 3 (i.e., n≥3).

In the reaction scheme depicted in Scheme 1 above, Z—(OH)$_n$ is the branched polyol starting material, with Z representing the branched part of the polyol consisting of a hydrocarbon backbone with n branches which are preferably chains having ether linkages. Preferably, Z has the structure of Formula 2, as shown above. As a polyol (Z—(OH)$_n$), it is preferred to use a polyol in which the number of hydroxyl groups is not less than 3, or a mixture of such polyols. According to one embodiment, the polyols to be used according to the present invention are polyether polyols. This class of polyols is obtained by the ring-opening addition reaction of one or more alkylene oxides (e.g., ethylene oxide and propylene oxide) with a suitable reactant containing active hydrogen atoms, such as alcohols, amines and acids; more specifically, said reactant may be selected from the group consisting of triols, novolac resins, pentaerythritol, sorbitol, sucrose, diethylenetriamine and the like. Preferred starting materials are selected from the group consisting of:

Glycerol-ethoxylated polyether polyol {where in Formula 2, n equals 3 and R is O—[$CH_2$—$CH_2$—O]$_m$—$CH_2$—$CH_2$}, also known as ethoxylated glycerol or glycerol-ethylene oxide polymer; and Glycerol-propoxylated polyether polyol {where in Formula 2, n equals 3, and R is O—[$CH_2$—$CH(CH_3)$—O]$_m$—$CH_2$—$CH(CH_3)$}, also known as propoxylated glycerol or glycerol-propylene oxide polymer.

Polyester-polyols may also be used as starting materials according to the present invention; this class of polyols is obtained by the condensation reaction of dicarboxylic (or polycarboxylic) acid, such as adipic acid, phthalic acid or the like, with triols.

The novel compounds of the invention are useful as flame retardants. To reduce their viscosity, the new flame retardants may be used as a mixture with either a non-halogenated polyol, or a halogenated polyol, or a mixture thereof. More preferable are compositions of the new polymeric flame retardants with an ester of a pentavalent acid of phosphorus, namely, an ester of phosphoric acid. It is preferred to use for rigid polyurethane (PU) and polyisocyanurate (PIR) foams a halogenated, and more specifically, chlorinated alkyl phosphate esters. Particularly preferred are the triesters—trialkyl phosphates—such as tri(monochloroalkyl) phosphate or tri(dichloroalkyl) phosphate, with tris(2-chloropropyl)phosphate being especially preferred. The term "alkyl" preferably refers to a $C_1$-$C_5$ alkyl. It should be noted that the phosphate ester may be either symmetric or asymmetric, containing identical or different alkyl groups, respectively. It is preferred to use for flexible PU foams a halogen-free esters of phosphoric acid, and more specifically, butylated triphenyl phosphate esters. Particularly preferred is Phosflex 71 B, which is a mixture of t-butylphenyl diphenyl phosphate, bis(t-butylphenyl)phenyl phosphate, triphenyl phosphate and tri(t-butylphenyl) phosphate.

The composition of the novel compounds of Formula 1 with either halogenated or non-halogenated esters of phosphoric acid (or both), forms another aspect of the invention. The weight ratio between the compound of Formula 1 and the ester of phosphoric acid in the flame-retardant composition of the invention is between 1:9 and 9:1, e.g., the concentration of the (optionally halogenated) phosphoric acid ester relative to the total weight of the composition is preferably between 10 and 90%, and more preferably between 30 and 70%. Other brominated flame retardants, for example tribromoneopentyl alcohol (FR-513) may be included in the composition of the invention, such that the weight concentrations of the compound of Formula 1, the (optionally halogenated) phosphoric acid ester and tribromoneopentyl alcohol in the flame-retardant composition of the invention are in the ranges from 10 to 50 wt %, 10 to 50 wt % and 10 to 50 wt %, respectively.

All the above and other characteristics and advantages of the invention will be better understood through the following illustrative and non-limitative detailed description of the preferred embodiments thereof.

DETAILED DESCRIPTION OF PREFERRED EMBODIMENTS

A mixture of pentabromobenzyl moiety-containing hydroxy-functional compounds of the present invention is prepared by the reaction of a pentabromobenzyl halide, preferably bromide (PBBBr) with a polyol (Scheme 1). It is preferred to use a polyol in which the number of hydroxyl groups is not less than 3, or a mixture of such polyols (or the corresponding metal alcoholate), in the presence or absence of a base.

Polyols used in the process for preparing the compounds of Formula I of the present invention include aliphatic polyether polyols having a molecular weight of 250-1000 or more (preferably from 400 to 700, e.g. 450 to 700), and a functionality of 3 or higher, such as those employed in the polyurethane industry, especially glycerol-based polyether polyols, for example: Alcupol C-5710—a glycerol initiated polyether polyol having a hydroxyl value of 250 mg KOH/g; Alcupol R-2510—a glycerol initiated polyether polyol having a hydroxyl value of 570 mg KOH/g; Voranol 450 or Voranol 700 which are glycerol initiated polyether polyols having molecular weight of about 450 or 700, respectively and Ucon Treg 500 from Dow.

In a preferred embodiment, the reaction of PBBBr and the polyol is carried out in the presence of a strong base such as sodium hydroxide or potassium hydroxide, in a medium of an organic solvent. The organic solvent is selected from aromatic compounds. Especially suitable aromatic solvents are xylene, chlorobenzene, ortho-dichlorobenzene, bromobenzene, mesitylene, and in particular, toluene.

The molar ratio between the polyol and the PBBBr is suitably adjusted such that at least one hydroxyl group of the polyol is replaced with PBBBr. It should be noted that the product may be in the form of a mixture, the components of which differ from one another with respect to the number of PBBBr and hydroxyl groups attached thereto (e.g. in the predominant component of the mixture $n_1$ equals 1 and $n_2$ equals 2, whereas in the minor component $n_1$ equals 2 and $n_2$ equals 1).

An effective amount of the base employed in the process is in a range of 1-1.2 mol per 1 mol PBBBr, and preferably 1.0-1.05 mol. The excess of base may lead to a side reaction to produce di-pentabromobenzyl ether.

The preferred reaction temperature is between 40 and 150° C., and preferably between 50° C. and 80° C.

The base (e.g., sodium or potassium hydroxide) is preferably employed in a solid form. Water should be eliminated from the reaction mixture to prevent the side reactions of PBBBr with water to produce pentabromobenzyl alcohol.

It should be noted that the reaction may also be conducted without a base at a temperature of between 150° C. and 250° C. However, in view of the fact that under such high temperatures the formation of undesired decomposition products may occur, it is generally preferred to carry out the reaction in the presence of a base.

Another aspect of the invention therefore relates to a process, which comprises reacting pentabromobenzyl halide, preferably bromide (PBBBr) with at least one polyol which contains not less than three hydroxyl groups, as described above. The process preferably comprises charging a reaction vessel with the polymeric polyol, a base and an organic solvent, heating the reaction mixture under reflux to remove water therefrom, adding pentabromobenzyl halide to the reaction mixture, maintaining same under heating and stirring to complete the reaction, and collecting the product of Formula 1.

The product is typically collected in the form of a mixture, generally a liquid mixture, comprising two or more compounds of Formula 1, wherein in a first compound $n_1 \geq n_2$ and in a second compound $n_1 < n_2$. Such a mixture forms another aspect of the invention.

The novel compounds of the present invention are highly efficient flame retardants when incorporated into rigid or flexible polyurethane foams, polyisocyanurate (PIR) foams, polyurethane coatings, polyurethane adhesives and polyurethane elastomers. It should be noted that the compounds of the invention are useful over a broad Isocyanate Index (abbreviated herein MDI or TDI). The index refers to the ratio of isocyanate practically used in the formulation vs. the theoretical stoichiometric amount of isocyanurate required, expressed in percents.

In view of the relatively high viscosity of the new bromine-containing polymeric flame retardants of the invention, these compounds are preferably used in the form of a mixture with less viscous halogen-free polyether polyols employed in the polyurethane industry.

Alternatively, the bromine-containing polyols of the invention can be used in the form of a mixture with less viscous halogen-free or halogen-containing alkyl phosphates such as tris-(chloropropyl) phosphate, tris-(dichloropropyl) phosphate or tris-(chloroethyl) phosphate.

The rigid polyurethane or polyisocyanurate foams contain a typical flame retardant amount of the composition of this invention. Typically, the compositions of this invention are used in amounts providing a total bromine concentration in the polymer in the range of 0.3 to 15 wt %, based on the total weight of the polymer. Preferably the total bromine concentration in the polymer is in the range 1 to 10 wt % and more preferably in the range of 2 to 5 wt %, based on the total weight of the polymer. Most preferably, the amounts used of the flame retardants of this invention are at least sufficient to meet the current requirements of the DIN 4102 B2 test.

The flexible polyurethane foams contain a typical flame retardant amount of the composition of this invention. Typically, the compositions of this invention are applied in amounts that provide a total bromine concentration in the polymer in the range of 0.3 to 15 wt %, based on the total weight of the polymer. Preferably the total bromine concentration in the polymer is in the range of 1 to 10 wt % and more preferably in the range of 1.5 to 5 wt %, based on the total weight of the PU polymer. Most preferably, the amounts used of the flame retardants of this invention are at least sufficient to meet the current requirements of the CAL Technical Bulletin 117 Section A.

EXAMPLES

Example 1

Into a 1 L flask fitted with a mechanical stirrer, thermometer, condenser, $N_2$ injector and Dean-Stark trap were placed a three-functional, glycerol-based polyether polyol with molecular weight ~1000 (500 g, 0.5 mol), NaOH (28 g, 0.7 mol) and toluene (700 ml). The mixture was heated under reflux (116° C.) for 10 h until all the water was removed (~12 g). After that, the temperature was allowed to cool to 40° C. PBBBr (396 g, 0.7 mol) was added in portions. The mixture was vigorously stirred at 70° C. for 2 h until no PBBBr was detected (GC). After the PBBBr had disappeared, $H_3PO_4$ was added to reach pH~7. The solid was filtered off, the toluene was evaporated and the product was washed with water 3 times at 70° C. After drying at 90° C. under reduced pressure 792 g (~92% yield) of liquid product were obtained.
Total Br=32.2%; OH number=70.5 mg KOH/g.

Example 2

Into a 0.5 L flask fitted with a mechanical stirrer, thermometer, condenser, $N_2$ injector and Dean-Stark trap were placed a three-functional, glycerol-based polyether polyol with a molecular weight ~300 (9.8 g, 33.3 mmol), KOH (3.7 g, 66 mmol) and toluene (300 ml). The mixture was heated under reflux (116° C.) for 1.5 h until all the water was removed. After that, temperature was allowed to cool to 90° C. PBBBr (37.7 g, 66 mmol) was added in portions. The mixture was vigorously stirred at 90° C. for 2.5 h until no PBBBr was detected (GC). After the PBBBr disappeared, $H_3PO_4$ was added to reach pH~7. The solid was filtered off and the toluene solution was washed with water 2 times. The solvent was evaporated under reduced pressure to give product (35.4 g, 84% yield).
Total Br=58.3%, OH Number=93.2 mg KOH/g.

Example 3

Into a 1 L flask fitted with a mechanical stirrer, thermometer, condenser, $N_2$ injector and Dean-Stark trap were placed a three-functional, glycerol-based polyether polyol with molecular weight ~300 (180 g, 0.6 mol), NaOH (29.3 g, 0.73 mol) and toluene (550 ml). The mixture was heated under reflux (116° C.) for 8 h until the water was removed. After that, the temperature was allowed to cool to 40° C. PBBBr (407.5 g, 0.72 mol) was added in portions. The mixture was vigorously stirred at 70° C. for 2 h until no PBBBr was detected (GC). After the PBBBr had disappeared, $H_3PO_4$ was added to reach pH~7. The solid was filtered off, the toluene was evaporated and the product was washed with water 3 times at 70° C. After drying at ~90° C. under reduced pressure 476 g (~90% yield) of liquid viscous product were obtained.
Total Br=56.3%; OH number=102 mg KOH/g.

Example 4

Into a 1 L flask fitted with a mechanical stirrer, thermometer, condenser, $N_2$ injector and Dean-Stark trap were placed a three-functional, glycerol-based polyether polyol with molecular weight ~300 (180 g, 0.6 mol), NaOH (28.1 g, 0.7 mol) and toluene (550 ml). The mixture was heated under reflux (116° C.) for 8 h until the water was removed. After that, the temperature was allowed to cool to 40° C. PBBBr (391 g, 0.69 mol) was added in portions. The mixture was vigorously stirred at 70° C. for 2 h until no PBBBr was detected (GC). After the PBBBr had disappeared, $H_3PO_4$ was added to reach pH~7. The solid was filtered off, the toluene was evaporated and the product was washed with water 3 times at 70° C. After drying at ~90° C. under reduced pressure 462 g (~90% yield) of liquid viscous product were obtained.
Total Br=56.9%; OH number=100 mg KOH/g.

Example 5

Into a 1 L flask fitted with a mechanical stirrer, thermometer, condenser, $N_2$ injector and Dean-Stark trap were placed a three-functional, glycerol-based polyether polyol with molecular weight ~300 (180 g, 0.6 mol), NaOH (30.5 g, 0.76 mol) and toluene (550 ml). The mixture was heated under reflux (116° C.) for 8 h until the water was removed. After that, the temperature was allowed to cool to 40° C. PBBBr (424.5 g, 0.75 mol) was added in portions. The mixture was vigorously stirred at 70° C. for 2 h until no PBBBr was detected (GC). After the PBBBr had disappeared, $H_3PO_4$ was added to reach pH~7. The solid was filtered off, the toluene was evaporated and the product was washed with water 3 times at 70° C. After drying at ~90° C. under reduced pressure 441 g (~81% yield) of liquid viscous product were obtained.
Total Br=55.4%; OH number=98 mg KOH/g.

Example 6

Into a 0.5 L flask fitted with a mechanical stirrer, thermometer, condenser, $N_2$ injector and Dean-Stark trap were placed glycerol based polyol with MW~670 (Alcopol 2510, 67.3 g, 0.10 mol), NaOH (12.0 g, 0.3 mol) and toluene (200 ml). The mixture was heated under reflux (116° C.) for 3 h until all the water was removed. After that, the temperature was allowed to cool to 70° C. PBBBr (145.8 g, 0.257 mol) was added in portions. The mixture was vigorously stirred at 70° C. for 2 h until no PBBBr was detected (GC). After the PBBBr had disappeared, $H_3PO_4$ was added to reach pH~7. The solid was filtered off. The solvent was evaporated under reduced pressure to give the product (124 g, ~64% yield).
Total Br=48.3%; OH number=48.1 mg KOH/g.

Example 7

Into a 0.5 L flask fitted with a mechanical stirrer, thermometer, condenser, $N_2$ injector and Dean-Stark trap were placed Alcopol 2510 (67.3 g, 0.10 mol), NaOH (8.0 g, 0.2 mol) and toluene (200 ml). The mixture was heated under reflux (116° C.) for 3 h until all the water was removed. After that, the temperature was allowed to cool to 70° C. PBBBr (97.2 g, 0.17 mol) was added in portions. The mixture was vigorously stirred at 70° C. for 2.5 h until no PBBBr was detected (GC). After the PBBBr had disappeared, $H_3PO_4$ was added to reach pH~7. The solid was filtered off. The solvent was evaporated under reduced pressure to give the product (125 g, ~83% yield).
Total Br=41.6%, OH number=79.9 mg KOH/g.

Example 8

Into a 1 L flask fitted with a mechanical stirrer, thermometer, condenser, $N_2$ injector and Dean-Stark trap were placed glycerol based polyol (Voranol 3008) with MW~3000 (300 g, 0.10 mol), KOH (12.3 g, 0.22 mol) and toluene (300 ml). The mixture was heated under reflux (116° C.) for 3.5 h until all the water was removed. After that, temperature was allowed to cool to 90° C. PBBBr (113 g, 0.2 mol) was added in portions. The mixture was vigorously stirred at 90° C. for 2 h until no PBBBr was detected (GC). After the PBBBr had disappeared, $H_3PO_4$ was added to reach pH~7. The solid was filtered off and the toluene was evaporated under reduced pressure to give the product (221 g, ~60% yield).
Total Br=11.6%. OH number=22.9 mg KOH/g.

Example 9

Reactor under N$_2$ atmosphere, equipped with a mechanical stirrer, a thermometer and Din-Starck equipment was charged with the glycerol based ethoxylated polyether polyol Ucon Treg (200.0 g, 0.4 mol), NaOH (19.2 g, 0.48 mol) and toluene (600 ml). The reactor contents were heated under reflux for ~3 h, until water (~9 g) was evaporated. Mixture was cooled to 50° C. and PBBBr (271.4 g, 0.48 mol) was added in one portion. The resulting mixture was heated for 2 hours at 70-75° C. until the PBBBr conversion was completed. About 0.5-0.6 g of H$_3$PO$_4$ (85%) was added to give pH=7, then non-soluble compounds were filtered off and toluene was evaporated under reduced pressure at 80° C. to give viscous liquid. Obtained product was washed with water (230 ml×3) at ~75° C. and traces of water were distilled off under reduced pressure to obtain 380 g viscous liquid. Total Br=49.3%; OH number=67 mg KOH/g.

The application of the new compounds of the present invention is demonstrated through their use as flame retardants in standard formulations for rigid polyurethane foams (Examples 10-13), for rigid polyisocyanurate foams that have MDI Index of 200% (Examples 14-17), and for rigid polyisocyanurate foams with MDI Index of 350%—(Examples 18-21). In addition to the flame retardant, the following components were used in the preparation of the foams:

Polyol Components Used for PUR Production:
1. Terol 516—Polyester polyols having a hydroxyl value of 305 mg KOH/g.
2. Fox-O-Pol M530—polyol having a hydroxyl value of 530 mg KOH/g.
3. Glycerol.

Polyol Components Used for PIR (200% Index) Production:
1. Terol 516—Polyester polyols having a hydroxyl value of 305 mg KOH/g.
2. DEG—diethyleneglycol Polyol Components Used for PIR (350% Index) Production:
1. Kosa Terate 2541—polyol having a hydroxyl value of 234 mg KOH/g.

Ancillary Chemicals

| | |
|---|---|
| DMCHA | dimethylcyclohexylamine |
| PMDETA | methylbis(2-dimethylaminoethyl)amine |
| Dabco K-15 | catalyst |
| AM 58 | trimerisation catalyst |
| DC 193 | silicone surfactant |
| TCPP | tris(chloropropyl)phosphate |
| Pentane | blowing agent |
| Dabco TMR30 | Amine catalyst |
| Tegostab B8460 | silicone surfactant |
| Kosmos 75 | catalyst (potassium-2-ethyl hexanoate) |

Isocyanate
MDI—polymeric diphenylmethane diisocyanate

Examples 10-13

Process for Preparing Rigid Polyurethane Foams Using the Flame Retardant Compositions The procedure for the foam preparation was as follows:
The polyols, water, surfactant, flame retardant (abbreviated "FR" in the tables below) and catalysts were weighed and placed in a mixing beaker and mixed to form a homogeneous solution. To this solution was added pentane, and after additional mixing, the polymeric isocyanate. The mixture was stirred at 20° C. under 3000 rpm for 6 sec and poured into another beaker. The foam that formed was kept for at least 24 hr at room temperature and then removed from the beaker and cut into test specimens with a saw. The samples were then tested for flammability according to the DIN 4102 B2 test procedure (a flame height of 15.0 cm or less means that the foam has passed the test). Table 1 summarizes the ingredients and parameters for the foam preparation and the results of the tests.

TABLE 1

Pentane-blown B2 continuous system (mixed at 20° C.)

| Composition (g) | Example 10 | Example 11 | Example 12 | Example 13 |
|---|---|---|---|---|
| M530 | 27 | 27 | 27 | 27 |
| Terol 516 | 27 | 27 | 27 | 27 |
| Glycerol | 12 | 12 | 12 | 12 |
| FR of Example 4/TCPP 70:30 | 40 | | | |
| FR of Example 4/TCPP 60:40 | | 40 | | |
| FR of Example 4/FR-513/TCPP 50:20:30 | | | 40 | |
| FR of Example 4/FR-513/TCPP 50:10:40 | | | | 40 |
| TCPP | 20 | 20 | 20 | 20 |
| DMCHA | 2 | 2 | 2 | 2 |
| AM58 | 1 | 1 | 1 | 1 |
| DC193 | 1.5 | 1.5 | 1.5 | 1.5 |
| Water | 2.49 | 2.49 | 2.49 | 2.49 |
| Pentane | 13.2 | 13.2 | 13.2 | 13.2 |
| Total | 146.19 | 146.19 | 146.19 | 146.19 |
| Isocyanate, g (Urestyl-10) | 175.42 | 173.61 | 176.99 | 174.6 |
| Mix time, sec | 6 | 6 | 6 | 6 |
| Cream time, sec | 12 | 11 | 11 | 12 |
| Gel time, sec | 33 | 32 | 30 | 32 |
| Tack free time, sec | 43 | 42 | 41 | 36 |
| Cure time, sec | 74 | 84 | 73 | 94 |
| Br content in polyol mixture, wt % | 10.9 | 9.4 | 11.8 | 9.8 |
| Br content in foam, wt % | 5.0 | 4.3 | 5.3 | 4.5 |
| Flame height, cm (DIN 4102) | 10.8 | 9.3 | 10.8 | 8.4 |

Examples 14-17

Process for Preparing Rigid Polyisocyanurate Foams (PIR, MDI Index 200%) Using the Flame Retardant Compositions The procedure for the foam preparation was as follows:
The polyols, water, surfactant, flame retardant and catalysts were weighed and placed in a mixing beaker, and mixed to form a homogeneous solution. To this solution was added pentane, and after further mixing the polymeric isocyanate, then the mixture was stirred at 20° C. under 3000 rpm for 6 sec and poured into another beaker. The foam that formed was kept for at least 24 hr at room temperature and then removed from the beaker and cut into test specimens with a saw. The samples were then tested for flammability according to the DIN 4102 B2 test procedure (a flame height of 15.0 cm or less means that the foam has passed the test). Table 2 summarizes the ingredients and parameters for the foam preparation and the results of the testing of the foams.

TABLE 2

Pentane-blown B2 system (mixed at 20° C.)

| Composition (g) | Example 14 | Example 15 | Example 16 | Example 17 |
|---|---|---|---|---|
| Terol 516 | 100 | 100 | 100 | 100 |
| DEG | 5 | 5 | 5 | 5 |
| FR of Example 4/TCPP 70:30 | 20 | | | |
| FR of Example 4/TCPP 50:50 | | 20 | | |
| FR of Example 4/FR-513/TCPP 50:20:30 | | | 20 | |
| FR of Example 4/FR-513/TCPP 40:10:50 | | | | 20 |
| TCPP | 40 | 40 | 40 | 40 |
| PMDETA | 0.5 | 0.5 | 0.5 | 0.5 |
| K15 | 2 | 2 | 2 | 2 |
| DC 193 | 1.5 | 1.5 | 1.5 | 1.5 |
| Water | 2 | 2 | 2 | 2 |
| Pentane | 14 | 14 | 14 | 14 |
| Total | 185 | 185 | 185 | 185 |
| Isocyanate, g | 241.9 | 239.6 | 243.34 | 240.36 |
| Mix time, sec | 6 | 6 | 6 | 6 |
| Cream time, sec | 10 | 12 | 12 | 13 |
| Gel time, sec | 42 | 48 | 47 | 48 |
| Tack free time, sec | 62 | 83 | 63 | 82 |
| Br content in polyol mixture, wt % | 4.2 | 3.1 | 4.7 | 3.3 |
| Br content in foam, wt % | 1.8 | 1.3 | 2.0 | 1.4 |
| Flame height, cm (DIN 4102) | 7.9 | 8.9 | 7.8 | 8.3 |

Examples 18-21

Process for Preparing Rigid Polyisocyanurate Foams with Index 350%

The procedure is the same as in the previously described examples.

Table 3 summarizes the ingredients and parameters of the foam preparation and the results of the testing of the foams.

TABLE 3

Pentane-blown B2 system (mixed at 20° C.)

| Composition (g) | Example 18 | Example 19 | Example 20 | Example 21 |
|---|---|---|---|---|
| Kosa Terate 2541 | 100 | 100 | 100 | 100 |
| FR of Example 2/TCPP 50:50 | 10 | | | |
| FR of Example 7/TCPP 70:30 | | 5 | | |
| FR of Example 6/TCPP 80:20 | | | 5 | |
| FR of Example 6/TCPP 70:30 | | | | 5 |
| TCPP | 10 | 15 | 15 | 15 |
| DMCHA | 1.5 | 1.5 | 1.5 | 1.5 |
| Dabco TMR30 | 1 | 1 | 1 | 1 |
| Tegostab B8460 | 1.5 | 1.5 | 1.5 | 1.5 |
| Kosmos 75 | 1 | 1 | 1 | 1 |
| Water | 1 | 1 | 1 | 1 |
| Pentane | 13 | 13 | 13 | 13 |
| Total | 139 | 139 | 139 | 139 |
| Isocyanate, g | 252.63 | 250.92 | 251.6 | 251.46 |
| Mix time, sec | 6 | 6 | 6 | 6 |
| Cream time, sec | 9 | 9 | 9 | 9 |
| Gel time, sec | 36 | 28 | 34 | 39 |
| Tack free time, sec | 109 | 119 | 144 | 118 |
| Br content in polyol mixture, wt % | 2.1 | 1.07 | 1.39 | 1.2 |
| Br content in foam, wt % | 0.74 | 0.38 | 0.49 | 0.42 |
| Flame height, cm (DIN 4102) | 8.1 | 8.0 | 7.5 | 7.4 |

It should be noted that throughout the examples, the notation FR/TCPP or FR/FR-513/TCPP indicate a binary composition comprising FR of the invention and TCPP, or a ternary composition comprising FR of the invention, FR-513 and TCPP, respectively, with the weight ratios between the ingredients in the compositions being identified by the figures x:y or x:y:z.

Examples 22-24

Flexible Polyurethane Foams

Foam Preparation Procedure

The low-density formulations set out in Table 4 below served for the preparation of the flame retardancy test foams in 45×45×30 cm cardboard boxes.

The raw materials and their relative amounts that were used for the foams preparation were:

Polyol Voranol 3008: 100 php

Flame retardant of the invention, blended with phosphated ester (Phosflex 71-B) at varying ratio—from 60/40 wt %, via 50/50 wt % and 40/60 wt %, down to 30/70 wt %, respectively: 16.0 php Si surfactant Niax L-650: 1.0 php Amine catalyst blend Dabco 33LV/BDE at a ratio of 3/1: 0.23 php Blowing agent $MeCl_2$: 10 php Tin catalyst T-9: 0.30 php TDI (Index 110%): 71.1 php All the ingredients, apart for the water and TDI, were successively weighed and added in the above given order, into 4 l disposable cup. The mixer was then stirred at 2100 rpm for 20 sec, then pre-weighed water was injected through a syringe, while stirring, into the cup and stirring continued for another 20 sec. Pre-weighed TDI was then added and the stirring continued for another 7 sec after which the mixture was poured into the box and allowed to rise. Foams were left for 48 hours in a hood to cure before any further processing.

Flammability Test Results in Flexible Polyurethane Foams

The flame retardancy was tested in low density foams (1.03 pounds per cubic feet). After 48 hours of curing in the hood, samples were cut and conditioned according to the specifications of the CAL 117A TB for flammability test.

The brominated polymeric flame-retardant of the invention of Example 3 was used in the foams preparation.

Table 4 presents the average char length of the test following different sample conditioning terms, vs. the composition of the brominated polymeric flame retardant blend in phosphated ester (Phosflex 71-B).

TABLE 4

CAL 117A test results of flexible low-density polyurethane foams, flame-retarded with brominated polymeric FR of the invention, applied blended with phosphated ester

| Example | Blend composition: Br-Polymeric FR/Phosflex 71-B, ratio | Blend load, php | CAL 1 117A Average char length, cm | |
|---|---|---|---|---|
| | | | 104° C. conditioning | 22° C., 50% R.H. conditioning |
| 22 | 40/60 | 16.0 | 9.5 | 9.6 |
| 23 | 35/65 | 16.0 | 8.9 | 8.7 |
| 24 | 30/70 | 16.0 | 9.6 | 9.9 |

The invention claimed is:

1. A compound of Formula 1:

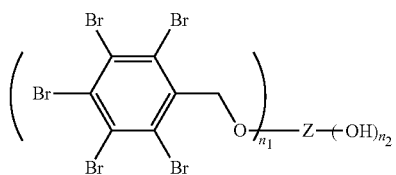

Formula 1 wherein each of $n_1$ and $n_2$ is an integer equal to or greater than 1, with the sum $(n_1+n_2)$ being equal to or greater than 3, and Z is a moiety derived from a branched polyol containing n chains, with $n=n_1+n_2$, wherein each chain comprises not less than 3 repeating units, wherein the repeating unit is an alkylene oxide unit or [CO—($C_2$-$C_5$)alkylene-O] unit.

2. The compound according to claim 1, wherein the chains are selected from the group consisting of:
O—[($C_2$-$C_3$)alkylene-O]$_m$—($C_2$-$C_3$)alkylene and
O—[CO—($C_2$-$C_5$)alkylene-O]$_m$—($C_2$-$C_5$)alkylene,
m≥3, and n is an integer from 3 to 6.

3. The compound according to claim 2, wherein n=3 and the chains are O—[($C_2$-$C_3$)alkylene-O]$_m$—($C_2$-$C_3$)alkylene.

4. The compound according to claim 3, wherein the chains are O—[$CH_2$—$CH_2$—O]$_m$—$CH_2$—$CH_2$—.

5. The compound according to claim 3, wherein the chains are O—[$CH_2$—$CH(CH_3)$—O]$_m$—$CH_2$—$CH(CH_3)$—.

6. The compound according to claim 4, having three chains, wherein two chains are terminated with pentabromobenzyl group and one chain is terminated with hydroxyl group, said compound being represented by the following formula:

$CH_2$—O—[$CH_2$—$CH_2$—O]$_m$—$CH_2$—$CH_2$—O—$CH_2$—$C_6Br_5$.

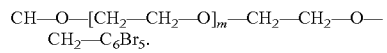

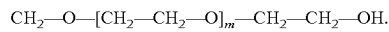

$CH_2$—O—[$CH_2$—$CH_2$—O]$_m$—$CH_2$—$CH_2$—OH.

7. A mixture comprising two or more compounds of claim 1, wherein in a first compound $n_1 \geq n_2$ and in a second compound $n_1 < n_2$.

8. A process for preparing the compound of Formula 1 as defined in claim 1, comprising reacting pentabromobenzyl halide with branched polyol of the formula Z(OH)n, which contains n chains with n terminal hydroxyl groups wherein n≥3, optionally in the presence of a base, and forming the compound of Formula 1 as defined in claim 1.

9. The process according to claim 8, wherein the pentabromobenzyl halide is pentabromobenzyl bromide, said process being carried out in the presence of a base which is either sodium hydroxide, potassium hydroxide or a mixture thereof.

10. The process according to claim 8, wherein the branched polyol Z(OH)n has a molecular weight of between 250 and 3000 Da.

11. The process according to claim 10, wherein the branched polyol Z(OH)n comprises glycerol-based polyether polyol.

12. The process according to claim 11, wherein the glycerol-based polyether polyol is selected from the group consisting of glycerol-ethoxylated polyether polyol and glycerol-propoxylated polyether polyol.

13. A process, comprising charging a reaction vessel with a branched polymeric polyol, a base and an organic solvent, heating the reaction mixture under reflux to remove water therefrom, adding pentabromobenzyl halide to the reaction mixture, maintaining heating and stirring to complete the reaction, and collecting the compound of Formula 1 as defined in claim 1.

14. A flame retardant composition comprising the compound(s) of Formula 1 as defined in claim 1 and at least one ester of phosphoric acid.

15. The flame retardant composition according to claim 14, which further comprises tribromoneopentyl alcohol.

16. A polyurethane or polyisocyanurate composition flame-retarded with the compound of Formula 1 as defined in claim 1.

17. The polyurethane or polyisocyanurate composition according to claim 16, wherein the polyurethane or polyisocyanurate composition is selected from the group consisting of flexible polyurethane foam, rigid polyurethane foam and polyisocyanurate foam.

18. Flexible polyurethane foams flame-retarded with the compound of Formula 1 as defined in claim 1.

19. Rigid polyurethane foams flame-retarded with the compound of Formula 1 as defined in claim 1.

20. Polyisocyanurate foams flame-retarded with the compound of Formula 1 as defined in claim 1.

* * * * *